United States Patent
Larue et al.

(10) Patent No.: US 11,653,604 B2
(45) Date of Patent: May 23, 2023

(54) CROSS POLLINATION THROUGH LIQUID-MEDIATED DELIVERY OF POLLEN TO ENCLOSED STIGMAS OF FLOWERS FROM RECIPIENT PLANTS

(71) Applicant: MONSANTO TECHNOLOGY LLC, St. Louis, MO (US)

(72) Inventors: Huachun Wang Larue, Chesterfield, MO (US); Li Lin, St. Louis, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/589,926

(22) Filed: Oct. 1, 2019

(65) Prior Publication Data
US 2021/0092920 A1    Apr. 1, 2021

(51) Int. Cl.
*A01H 1/02* (2006.01)
*C12Q 1/6876* (2018.01)

(52) U.S. Cl.
CPC ............. *A01H 1/02* (2013.01); *C12Q 1/6876* (2013.01); *C12Q 2600/158* (2013.01)

(58) Field of Classification Search
None
See application file for complete search history.

(56) References Cited

U.S. PATENT DOCUMENTS

| 6,723,680 B2 | 4/2004 | Chung et al. |
| 10,076,091 B2 | 9/2018 | Brown |
| 2013/0118067 A1 | 5/2013 | Cope et al. |
| 2014/0289909 A1* | 9/2014 | Byrum ............... A01H 5/10 800/312 |
| 2017/0042102 A1 | 2/2017 | Safreno |
| 2017/0238535 A1 | 8/2017 | Cope et al. |
| 2018/0177752 A1 | 6/2018 | Heller et al. |
| 2020/0296954 A1 | 9/2020 | Cope et al. |
| 2021/0307273 A1 | 10/2021 | Boyer et al. |
| 2022/0279778 A1 | 9/2022 | Boyer et al. |

(Continued)

FOREIGN PATENT DOCUMENTS

| CN | 101617619 | 11/2011 |
| CN | 102599046 A | 7/2012 |
| CN | 103642748 | 3/2014 |

(Continued)

OTHER PUBLICATIONS

Zeraatkar et al., 2013, "Preliminary evaluation of artificial pollination in pistachio using pollen suspension spray" Plant Knowledge Journal 2(3):94-98 (Year: 2013).*

(Continued)

*Primary Examiner* — Matthew R Keogh
*Assistant Examiner* — David R Byrnes
(74) *Attorney, Agent, or Firm* — Dentons US LLP; Chunping Li, Esq.

(57) ABSTRACT

The invention provides novel methods for liquid-mediated delivery of pollen grains to enclosed stigmas in recipient female flowers. For example, methods for liquid-mediated pollination are provided. The methods provided include collecting pollen from a donor plant, suspending the collected pollen in a liquid solution, and introducing said solution to an enclosed stigma of a recipient flower bud on a recipient plant, thereby pollinating the flower with the pollen from the donor plant.

21 Claims, 7 Drawing Sheets
Specification includes a Sequence Listing.

(56) References Cited

U.S. PATENT DOCUMENTS

| | | | |
|---|---|---|---|
| 2022/0338432 A1 | | 10/2022 | Larue et al. |
| 2022/0400637 A1 | | 12/2022 | Borrowman et al. |

FOREIGN PATENT DOCUMENTS

| | | | |
|---|---|---|---|
| CN | 104719128 A | | 6/2015 |
| CN | 109105250 A | * | 1/2019 |
| CN | 109105250 A | | 1/2019 |
| CN | 210202815 | | 3/2020 |
| CN | 212184594 | | 12/2020 |
| EP | 1785032 | | 5/2007 |
| KR | 20050078007 | | 8/2005 |
| WO | 2017180849 | | 10/2017 |
| WO | 2020055647 | | 3/2020 |

OTHER PUBLICATIONS

Walker et al., 1979. Comparison of emasculation and non-emasculation for hybridization of soybean. Crop Science. 19: 285-286 (Year: 1979).*

Graybosch and Palmer, 1988, "Male Sterility in Soybean—An Overview" American Journal of Botany (75(1): 144-156 (Year: 1988).*

Sakamoto et al., 2009. "Spray pollination as a labor-saving pollination system in Japanese pear (*Pyrus pyrifolia*(Burm.f.) Nakai): Development of the suspension medium", Scientia Horticulturae 119 (2009) 280-285 (Year: 2009).*

Crespel, Laurent and Mouchotte, Jaques, "Methods of Cross-Breeding", Reference Module in Life Sciences (Year: 2016).*

Xi et al. "Induction of 2n pollen by colchicine in Populus x popularis and its triploids breeding". Sciendo. 60: 155-160. (Year: 2010).*

Sakamoto et al., 2009. "Spray pollination as a labor-saving pollination system in Japanese pear (*Pyrus pyrifolia*(Burm.f.) Nakai): Development of the suspension medium", Scientia Horticulturae. 119: 280-285 (Year: 2009).*

Erickson, "Variability of Floral Characteristics Influences Honey Bee Visitation to Soybean Blossoms". Crop science. 15(6):767-771. (Year: 1975).*

International Search Report and Written Opinion regarding PCT Application No. PCT/US2019/054076, dated Dec. 30, 2019.

Bosch et al., "Pectin Methylesterase, a Regulator of Pollen Tube Growth", Plant Physiology, Jul. 2005, vol. 138, pp. 1334-1346.

Jayaprakash, "Pollen Germination in vitro", Pollination in Plants. Webpage [online], Jun. 6, 2018; Retrieved from the internet:<URL:https://www.intechopen.com/books/pollination-in-plants/pollen-germination-in-vitro>; pp. 82-96.

Loguercio "Pollen treatement in high osmotic potential: a simple tool for invitro preservation and manipulation of viability in gametophytic populations". Braziian Journal of Plant Physiology. Apr. 2002, 14(1):65-70.

Pierce Biotechnology, Inc., "Protein stability and storage". Webpage [online]. Aug. 2005. Retrieved from the Internet:<URL:http://www.indiana.edu/~lchenlab/protocol_files/protein_storage.pdf>.

Ali, et al., Identification of Potent Gametocides For Selective Induction of Male Sterility in Rice, Indian Journal of Genetics and Plant Breeding, (1999), 429-436, 59-4.

Clough and Bent, Floral dip: a simplified method for Agrobacterium-mediated transformation of *Arabidopsis thaliana*, Plant Journal, (1998), 735-743, 16-6.

Diaz and Garay, Simple Methods For In Vitro Pollen Germination and Pollen Preservation of Selected Species of the Genus, Agave, e-Gnosis [online], (2008), 1-7, 6-2, Universidad de Guadalajara, Guadalajara, Mexico.

Jain and Shivanna, Storage of Pollen Grains of Crotmaria Retusa in Oils, Sexual Plant Reproduction, (1990), 225-227, 3.

Mishra and Shivanna, Efficacy of Organic Solvents For Storing Pollen Grains of Some Leguminous Taxa, Euphytica, (1982), 991-995, 31-3.

Palmer, et al., Pollen Production in Soybeans With Respect to Genotype, Environment, and Stamen Position, Euphytica, (1978), 427-433, 27.

Peterson, et al., A Flower and Pod Staging System For Soybean, Annals of Botany, (1992), 59-67, 69-1.

Sakamoto, et al., Spray Pollination as a Labor-Saving Pollination System in Japanese Pear (*Pyrus pyrifolia*(Burm. F.) Nakai.): Development of the Suspension Medium, Scientia Horticulturae, (2009), 280-285, 119-3.

Talukdar and Shivakumar, Pollination Without Emasculation: An Efficient Method of Hybridization in Soybean (*Glycine max* (L.) Merrill), Current Science, (2012), 628-630, 103-6.

Wood, et al., "Flight of the Robobees," Scientific American, Mar. 2013.

Yang, et al., Ovary-Drip Transformation: A Simple Method For Directly Generating Vector-And Marker-Free Transgenic Maize (*Zea mays* L.) With A Linear GFP Cassette Transformation, Planta, (2009), 793-801, 229-4.

Yano, et al., The Use of Liquid Pollen Extender Thickened With Polysaccharides For Artificial Pollination of Kiwifruit, Acta Horticulturae, (2007), 415-424, 753.

Zhao, et al., Pollen Magnetofection For Genetic Modification With Magnetic Nanoparticles as Gene Carriers, Nature Plants, (2017), 956-964, 3-12.

U.S. Appl. No. 17/762,658, filed Mar. 22, 2022, Larue et al..

Broglia and Brunori, Synergistic effect of low temperature and high sucrose concentration on maize pollen viability in aqueous medium, Crop Sci., 34:528-9, 1994.

Coe, Liquid media suitable for suspending maize pollen before pollination (abstract), Proceedings of the Missouri Academy of Science 3:7, 1966.

Hopping and Jerram, Supplementary pollination of tree fruits. I. Development of suspension media. NZ J. Agri. Res. 23:509-515, 1980.

Hopping and Jerram, Supplementary pollination of tree fruits. II. Field trials on kiwifruit and Japanese plums. NZ J. Agri. Res. 23:517-521, 1980.

Hopping and Simpson, Supplementary pollination of tree fruits. II. Suspension media for kiwifruit pollen. NZ J. Agri. Res. 25:245-250, 1982.

International Search Report and Written Opinion regarding International App. No. PCT/US21/25357, dated Aug. 11, 2021.

Johnson and Bernard, Soybean genetics and breeding, Advances in Agronomy 14:149-221, 1962.

Pfahler, In vitro germination and pollen tube growth of maize (*Zea mays* L.) pollen. I. calcium and boron effects, Canadian Journal of Botany 45(6):839-845, 1967.

Sadamori et al., Studies on the commercial hand pollination methods of apple flowers. I. Examination of pollen dilutes, of degree of pollen dilution and of pollinating methods. Bull. Tohoku Natl. Agric. Exp. Stn. 14:74-81, 1958.

Automatic & Air Atomizing Spray Nozzles. Spraying Systems Co. p. 78, (2018).

Ching. Controlled Pollination of Douglas fir: A Pictorial Manual on Technique, Forest Lands Research, Oregon Forest Research Center, Corvalis, 1960.

International Search Report and Written Opinion regarding International Application No. PCT/US22/18641, dated May 23, 2022.

Pacini, et al. Pollen Developmental Arrest: Maintaining Pollen Fertility in a World With a Changing Climate. Front. Plant Sci., May 24, 2019.

Rauf, et al. Advances in Plant Breeding Strategies: Agronomic, Abiotic and Biotic Stress Traits. Springer, Cham. 2016.

U.S. Appl. No. 17/680,781, filed Feb. 25, 2022, Boyer, et al.

Office Action regarding Chinese App. No. 2019801010656, dated Feb. 16, 2023.

* cited by examiner

Control seed set of conventional pollination using ms6 male sterile plants

Seed set of liquid pollination using ms6 male sterile plants

Control seed set of conventional pollination using male fertile plants

Seed set of liquid pollination using male fertile plants

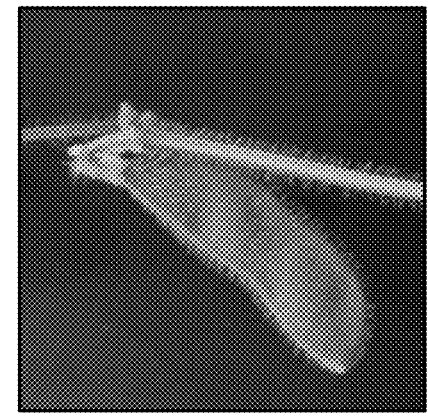
FIG. 7C Seed set of Maleic Hydrazide treated plants by cross-pollination
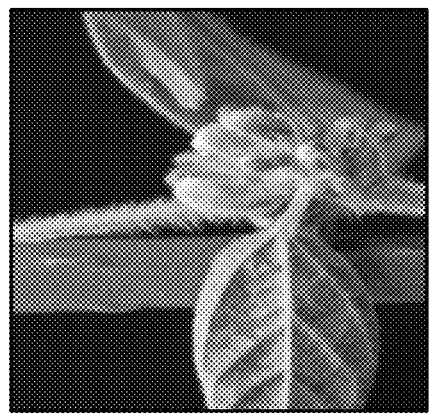
FIG. 7B Maleic Hydrazide treated plants
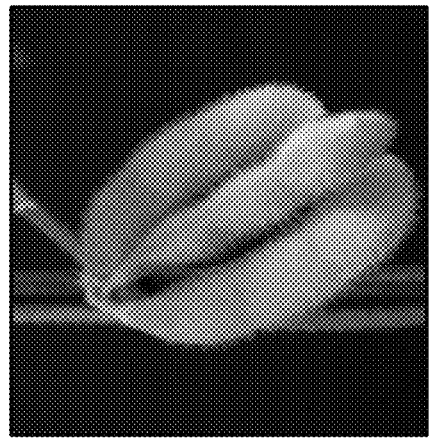
FIG. 7A Seed set of male fertile plants

CROSS POLLINATION THROUGH LIQUID-MEDIATED DELIVERY OF POLLEN TO ENCLOSED STIGMAS OF FLOWERS FROM RECIPIENT PLANTS

FIELD OF THE INVENTION

The present disclosure relates to the field of agricultural biotechnology, and more specifically to methods of improving cross-pollination efficiency via liquid-mediated delivery of donor plant pollen grains to enclosed stigmas of flowers from recipient plants.

INCORPORATION OF SEQUENCE LISTING

The sequence listing that is contained in the file named "MONS456US_ST25.txt," which is 12 kilobytes as measured in Microsoft Windows operating system and was created on May 30, 2019, is filed electronically herewith and incorporated herein by reference.

BACKGROUND OF THE INVENTION

Hybridization is an important aspect in the breeding of domesticated plants as it enables the introduction of transient hybrid vigor, desirable variation among different germplasms, transgenic trait integration, and generate novel phenotypes (Goulet et al., 2017). Plant breeders use hybridization or controlled cross pollination as the starting point of a breeding cycle in different crops. Conventional methods for cross pollination of many crop species, such as soybean, typically involve conventional pollination, which entails manual removal of the sepal and petals carefully with tweezers to expose the stigma of the flower. This process is complex, time consuming, and labor-intensive due to the anatomy and size of the flowers (Walker et al., 1979; Talukdar et al., 2012). Typical commercial breeding programs require thousands or even millions of crosses in workflows such as, development crosses, backcrosses, and trait integration. As breeders look to accelerate crop variety development and reduce labor needs, it is critical to develop improved crossing methods that facilitate a higher throughput and improve efficiency.

SUMMARY

In one aspect, the invention provides a method for liquid-mediated delivery of pollen to an enclosed stigma of a plant comprising the steps of: a) obtaining pollen from a donor plant; b) producing a liquid solution comprising said pollen; and c) introducing said solution to enclosed stigmas of recipient flowers, thereby pollinating the flower with the pollen from the donor plant. In some embodiments, the pollen grains are obtained from a plurality of flowers from the donor plant. In other embodiments, the step of introducing said solutions to an enclosed stigma on a recipient plant comprises injecting the solution into the flower bud. In some embodiments, the method provided herein further comprises the step of selecting a progeny seed or plant that results from said pollination. In a further embodiment, the donor plant comprises an allele that facilitates selecting said progeny plant or seed.

In another aspect, the present invention provides a method for liquid-mediated delivery of pollen to an enclosed stigma of a plant comprising the steps of: a) obtaining pollen from a donor plant; b) producing a liquid solution comprising said pollen; and c) introducing said solution to enclosed stigmas of recipient flowers, thereby pollinating the flower bud with the pollen from the donor plant and wherein the recipient flower bud is male sterile at the time of said pollinating. In some embodiments, the recipient plant is genetically male sterile. In some embodiments, the flower bud or recipient plant is treated with a gametocide resulting in male sterility. In some embodiments, the recipient plant is a soybean plant.

In yet another aspect, the present invention provides a method for liquid-mediated delivery of pollen to an enclosed stigma of a plant comprising the steps of: a) obtaining pollen from a donor plant; b) producing a liquid solution comprising said pollen; and c) introducing said solution to an enclosed stigma of a recipient flower, thereby pollinating the flower bud with the pollen from the donor plant; wherein the solution comprises at least a first component selected from the group consisting of a pectinase, a thickening agent, a surfactant, sucrose, mineral ions, a plant growth regulator, a carrier protein, and a nucleic acid molecule. In some embodiments, the at least a first component is a pectinase. In further embodiments the pectinase is a pectin methylesterase. In yet further embodiments, the solution comprises pectin methylesterase at a concentration of about 1.5 units/L to about 1500 units/L. In some embodiments, the at least a first component is a thickening agent. In further embodiments, the thickening agent is xanthan gum. In yet further embodiments, the solution comprises about 0.04% to about 0.08% xanthan gum by weight. In some embodiments, the at least a first component is a surfactant. In further embodiments, the surfactant is Tween 20. In yet further embodiments, the solution comprises about 0.001% to about 0.01% Tween 20 by weight. In some embodiments, the at least a first component is sucrose. In further embodiments, the solution comprises about 10% to about 20% sucrose by weight. In other embodiments, the at least a first component is a mineral ion. In further embodiments, the mineral ion is selected from the group consisting of $MgSO_4$, $ZnSO_4$, and boric acid. In yet further embodiments, the solution comprises about 0.01% to about 0.05% $MgSO_4$ by weight. In other embodiments, the solution comprises about 0.01% to about 0.05% $ZnSO_4$ by weight. In yet further embodiments, the solution comprises about 0.005% to about 0.02% boric acid by weight. In some embodiments, the at least a first component is a carrier protein. In other embodiments, the carrier protein comprises bovine serum albumin (BSA). In further embodiments, the solution comprises about 0.01% to about 0.1% bovine serum albumin (BSA) by weight.

In yet another aspect, the present invention provides a method for liquid-mediated delivery of pollen to an enclosed stigma of a plant comprising the steps of: a) obtaining pollen from a donor plant; b) producing a liquid solution comprising said pollen; and c) introducing said solution to an enclosed stigma of a recipient flower bud, thereby pollinating the flower bud with the pollen from the donor plant; wherein the method further comprises collecting seed resulting from said pollinating. In some embodiments, a progeny plant grown from said seed is crossed with itself or a second plant.

In yet a further aspect, the present invention provides a method for liquid-mediated delivery of pollen to an enclosed stigma of a plant comprising the steps of: a) obtaining pollen from a donor plant; b) producing a liquid solution comprising said pollen; and c) introducing said solution to an enclosed stigma of a recipient flower bud, thereby pollinating the flower bud with the pollen from the donor plant, wherein the method comprises creating an opening in said flower bud before introducing said solution. In some embodiments, the creating an opening comprises removing or rupturing an upper portion of said flower bud.

In another aspect, the present invention provides a method of producing a pollen suspension solution comprising a desired pollen concentration for cross-pollination comprising the steps of: a) collecting pollen-shedding flowers from a male parent; b) homogenizing said flowers to release pollen; c) purifying pollen from said homogenized flowers by removing floral debris; d) quantifying said purified pollen; and e) suspending said purified pollen in a solution to produce a pollen suspension solution comprising a desired pollen concentration. In some embodiments, said homogenizing comprises grinding said flowers in a bead mill homogenizer. In further embodiments, said homogenizing is performed with or without liquid. In some embodiments, the purified pollen is suspended in an 80% sucrose solution or in corn oil.

In yet another aspect, the present invention provides a method of producing hybrid seed comprising the steps of: a) obtaining pollen from a donor plant; b) producing a liquid solution comprising said pollen; c) introducing said solution to an enclosed stigma of a flower bud of a female recipient parent having a genotype that is different from that of the donor plant, thereby pollinating the female recipient flower with pollen from the donor plant; d) harvesting seed produced from said pollination; and e) identifying hybrid seed. In some embodiments, the donor plant is a soybean plant.

In another aspect, the present invention provides a method of producing an $F_1$ hybrid soybean seed comprising the steps of: a) preparing a pollen suspension solution comprising a desired pollen concentration from a donor soybean plant; b) introducing said pollen suspension solution to the enclosed stigma of a flower bud of a female parent having a genotype that is different from that of the donor plant, wherein said pollen suspension solution is introduced to the stigma by injecting said solution into the enclosed flower bud or by creating an opening in the flower bud and applying said solution into said opening, thereby pollinating the flower with pollen from the donor plant; and c) harvesting $F_1$ seed produced from said pollination. In some embodiments, the solution comprises at least a first component selected from the group consisting of a pectinase, a thickening agent, a surfactant, sucrose, a plant growth regulator, a mineral ion, a carrier protein, and a nucleic acid molecule. In other embodiments, the flower bud of the female parent is male sterile. In further embodiments, the $F_1$ seed is identified using phenotypic or genotypic markers.

BRIEF DESCRIPTION OF THE DRAWINGS

FIG. 1A shows the anatomy of a mature soybean flower where five petals enclose the pistil and ten stamens. FIG. 1B shows the mature androecium and gynoecium with shedding pollen and the nine stamens form a tube around the pistil while the tenth stamen remains free. FIG. 1C shows a representative flower bud suitable to serve as the recipient flower in cross-pollination. FIG. 1D shows details of the anatomy of a suitable recipient flower bud: the stigma becomes receptive to pollen while the anthers have not yet shed pollen.

FIG. 5A shows injection of pollen solution to flower buds. FIG. 5B shows application of a drop of pollen solution to a bud where the tip of the bud has been removed. FIG. 5C shows the cutting line above the stigma to remove the tip off the bud. FIG. 5D shows successful liquid delivery to stigma as indicated by red dye. Red dyes were included in the pollen solution as indicator of delivery of pollen solution to the stigma. Liquid pollen solution (20% sucrose, 0.04% xanthan gum, 15 U/L PME, 0.001% Tween 20 and pollen) with red dyes (Allura Red AC 0.01%) was injected into flower bud. After 5 min, the flower bud was dissected to check red stain on the stigma (indicated by arrow).

FIG. 6A shows images of control seed set in ms6 male-sterile plants cross pollinated with the conventional pollination technique. FIG. 6B shows images of seed set in ms6 male-sterile plants cross pollinated with donor pollen delivered in a liquid solution by injection. FIG. 6C shows images of control seed set in male-fertile recipient plants pollinated with the standard control pollination technique. FIG. 6D shows images of seed set in male-fertile plants cross pollinated with donor pollen delivered in a liquid solution by injection. In FIGS. 6C and 6D, marker-based genotyping was used to confirm the "hybrid" nature of the seeds set from the cross pollination.

FIGS. 7A, 7B, and 7C: Shows images of seed set when gametocide was used to induce male sterility. FIG. 7A shows a representative image of fertile plants bearing full seed set pod. FIG. 7B shows a representative image of fertile plants treated with 250 ppm maleic hydrazide to induce male sterility which resulted in no seed set without crossing. FIG. 7C shows a representative image of a seed pod resulting from flowers rendered male sterile by treatment with maleic hydrazide and subsequently cross-pollinated.

DETAILED DESCRIPTION

Figure 1A:
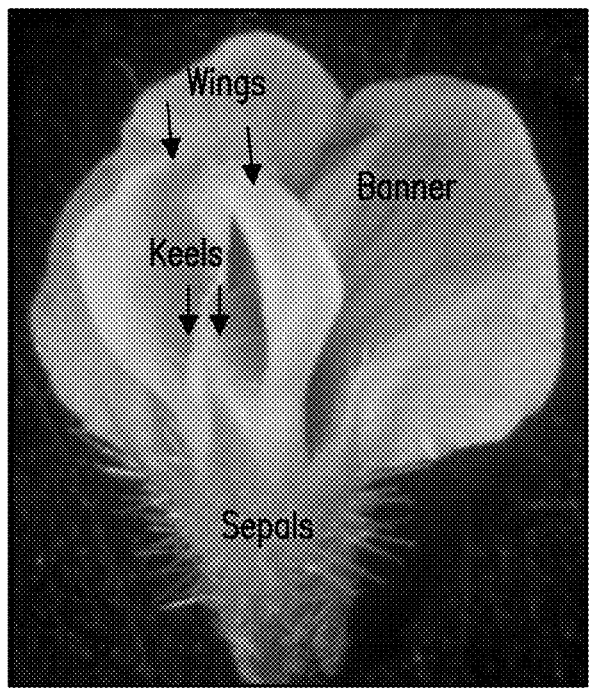
FIGS. 1A, 1B, 1C, and 1D: Show images of the anatomy of a mature soybean flower and exemplary recipient soybean flower bud.
Figure 1B:
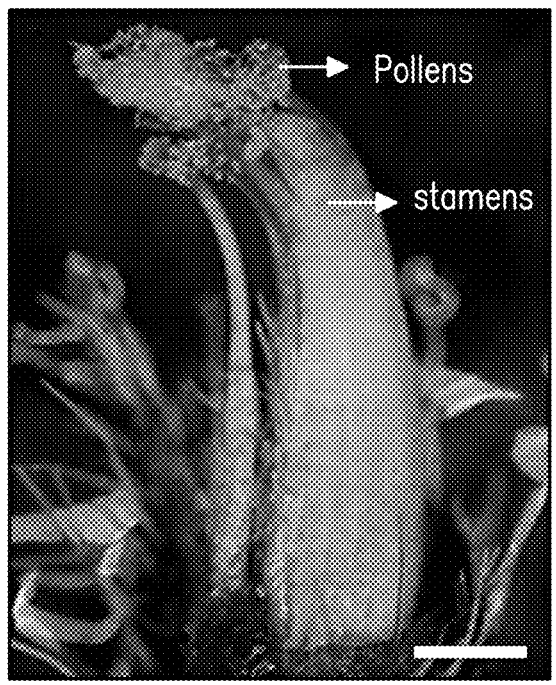

Modern plant breeding relies on outcrossing or cross-pollination to generate progeny plants having specific heritable traits that are obtained from each parental line. Therefore, throughput and efficiency have played an essential role in $F_1$ population development and trait integration workflow efficiency. Soybean (*Glycine max*) is an economically important agricultural crop, but its breeding has been hampered by a low efficiency process in controlled cross-pollination. Soybean belongs to the Papilionoideae subfamily of the Fabaceae family of flowering plants. Soybean flowers consist of five petals (one banner petal, two wing petals, and two keel petals) that enclose the pistil and ten stamens. Of the ten stamens, nine form a tube around the pistil while the tenth remains free. This structure results in the pollen from the anthers to be shed directly onto the stigma (FIGS. 1A and 1B). Typically, pollen is shed shortly before or immediately after the flower opens (anthesis), resulting in a high degree of self-pollination and rates of natural outcrossing is typically below 1% (Vollmann et al., 1992). Initially, soybean breeders performed hybridization through manual emasculation followed by pollination. About 50 years ago, the efficiency of the pollination approach was further improved through techniques that bypassed the emasculation step. Since then, this improved approach has remained the gold standard for soybean cross-pollination (Walker et al., 1979; Talukdar et al., 2012). However, this conventional pollination method is still very laborious and time-consuming, typically including the steps of: (1) removing sepals on a selected flower bud of a female parent; (2) removing petals one by one to expose the stigma; (3) searching for bright, opened flowers on a male parent; (4) removing petals one by one until anthers are seen; and (5) rubbing the male donor parent's anthers onto female parent's stigma. The current invention represents a significant advancement in the art in that it surprisingly permits cross-pollination by liquid-mediated delivery of pollen to enclosed stigmas of flowers from recipient plants, thereby bypassing the need to manually remove the sepals and petals as done with conventional crossing techniques. As used herein "enclosed stigma" refers to a stigma on a flower that is still enclosed by flower structures such as petals and sepals at the time of crossing. To ensure a successful cross-pollination using the liquid-mediated pollen delivery system described herein, recipient female flowers must be used at the optimal developmental stage. At this stage, the stigma is receptive to pollen grains and the anthers have not yet shed pollen.

The present disclosure thus permits implementation of high throughput methods for the delivery of donor pollen to an enclosed stigma of a recipient flower. The methods provided herein substantially reduce the time and labor previously required to facilitate cross-pollination in soybean. This is of particular significance as modern plant breeding programs may require thousands or even millions of individual crosses on a yearly basis in order to produce a new plant variety with improved traits.

Liquid Pollination Solution Formulation

In one aspect, the present invention provides methods for obtaining pollen from a donor plant and producing a liquid solution comprising said pollen for further use in pollination. As used herein, "pollen" refers to at least one pollen grain and may comprise a plurality of pollen grains. In general, it will be desirable to use a solution containing ingredients that permit uniform pollen dispersal and maintain high viability of pollen grains in solution. Non-limiting examples of components that may be used in the production of such a solution are provided herein and may include, in certain embodiments, a pectinase, a thickening agent, a surfactant, sucrose, mineral ions, a plant growth regulator, and a nucleic acid molecule. In some embodiments, the thickening agent may be xanthan gum, which serves to uniformly disperse pollen in the solution and may, as one example, be in the solution at a concentration of about 0.04% to about 0.08% xanthan gum by weight. In some embodiments, the solution may be an aqueous solution or may be comprised in other solvents. In further embodiments, the solution can comprise sucrose, which serves as a regulator of osmotic stress, and may be in the solution at a concentration of, for example, about 10% to about 20% sucrose by weight. In some embodiments, the pectinase is pectin methylesterase (PME), which serves as a facilitator of pollen-stigma interaction, and may be in the solution at a concentration of, for example, about 1.5 units/L to about 1500 units/L. In some embodiments, the surfactant is Tween 20, which serves to improve liquid penetration, and may be in the solution at a concentration of, for example, about 0.001% to about 0.01% Tween 20 by weight. In certain embodiments, the solution comprises a plurality of soybean pollen grains and includes, but is not limited to, the following components: xanthan gum at about 0.04% to about 0.08% (w/v); sucrose at about 10% to about 20% (w/v); PME: at about 0.01 mg/L to about 10 mg/L; and Tween 20: at about 0.001% to about 0.01% (v/v). The solution may also include a carrier protein to stabilize the pectinase, such as bovine serum albumin (BSA) at a concentration of about 0.1 mg/ml. A plant growth regulator may also be present, such as gibberellic acid (GA) at a concentration of about $10^{-5}$ M to about $10^{-8}$ M to regulate pollen germination and pollen tube growth; $MgSO_4$ at a concentration of about 0.01% to about 0.05% to support $Ca^{2+}$ uptake or binding; and $ZnSO_4$ at a concentration of about 0.01% to about 0.05% to promote pollen germination and pollen tube growth; boric acid at a concentration of about 0.005% to about 0.02% to regulate pollen germination and pollen tube growth.

The present invention also provides methods for collection and purification of donor pollen for use in the methods provided herein. In some embodiments, donor pollen is obtained by processing flowers containing pollen, thereby releasing the pollen. In a preferred embodiment, pollen is released from flowers by gently grinding the flowers using a bead mill homogenizer. The flowers may be ground using liquid or without liquid. The released pollen is purified to remove floral debris and spun to collect purified pollen grains. Once the pollen grains are purified, they may be resuspended in a pollination solution as described herein. Alternatively, the purified pollen grains may be resuspended in an 80% sucrose solution or in oil and stored at 4° C. or −20° C., respectively, or in similar conditions that preserve the viability of the pollen. In a preferred embodiment, collected soybean pollen grains are resuspended and stored in corn oil. Corn oil appears to be as effective in pollen preservation as cryopreservation, which are more expensive and cumbersome alternatives. It has been reported that mineral oil, soybean oil, and olive oil may be used for storage of pollen grains of *Crotalaria retusa* L. (Jain and Shivanna, 1990). In addition, some organic solvents do not extract membrane phospholipids and are highly suitable to the storage of pollen, such as benzene, petroleum, diethyle ether, cyclohexane, butanol, propanol (Mishra and Shivanna, 1982; Diaz et. al., 2007). In some embodiments, the purified pollen is quantified using, for example, a hemocytometer. This permits the addition of a pre-determined quantity of pollen grains to the pollination solution, thereby obtaining a desired density of pollen grains. One of skill in the art will appreciate in view of the present disclosure that the desired density level of pollen can be optimized for any specific recipient plant based on plant variety and environmental conditions using the methods disclosed herein.

Delivery of Pollen Solution for Pollination of Plants

Figure 1C:
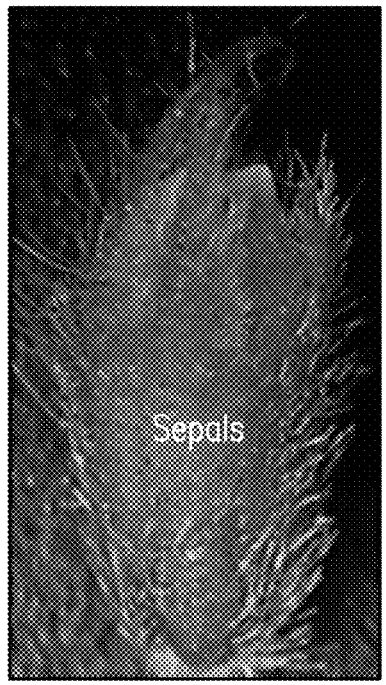
Figure 1D:
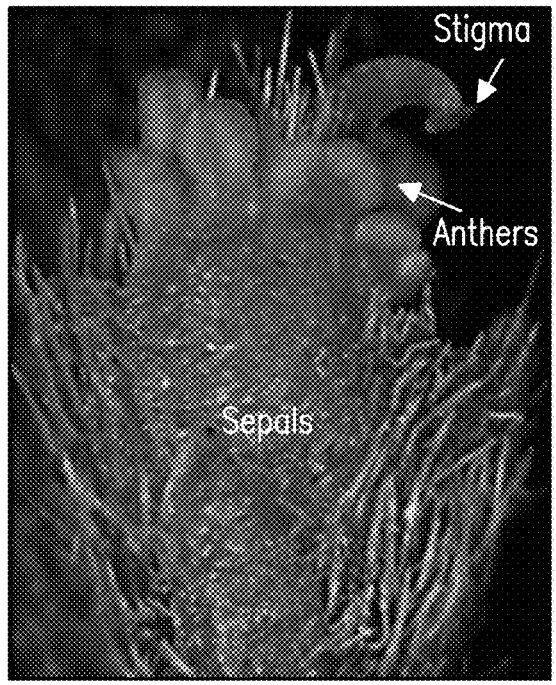

The present invention surprisingly permits cross-pollination of potentially any plant. In one embodiment, the method includes obtaining pollen from a donor plant, producing a liquid solution comprising the pollen, and introducing the solution into a flower bud on a recipient plant, thereby pollinating the flower with the pollen from the donor plant. In certain aspects, an optimum developmental stage for delivery of the pollination solution to flower buds may be determined. This can be determined empirically using the methods described herein. To promote cross-pollination, it is preferable to deliver the liquid solution containing pollen grains to a recipient flower during a specific time period in which the stigma becomes receptive to pollen and the anthers have not yet shed pollen. In soybean, it was found that around the B1 stage of flower bud development was effective for cross-pollination (Peterson et al., 1992). At this stage, the corolla is visible, but not fully extended beyond the calyx lobes in the flower bud, and the stigma is enclosed by petals and sepals (FIGS. 1C and 1D).

Figure 5C:
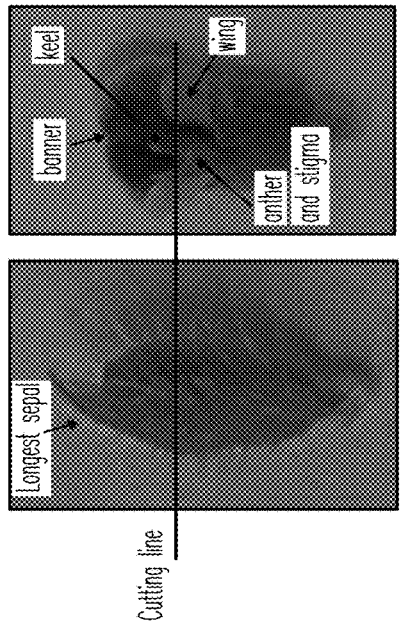
FIGS. 5A, 5B, 5C, and 5D: Show images of exemplary methods for liquid-mediated delivery of pollen to enclosed stigmas of flowers.
Figure 5B:
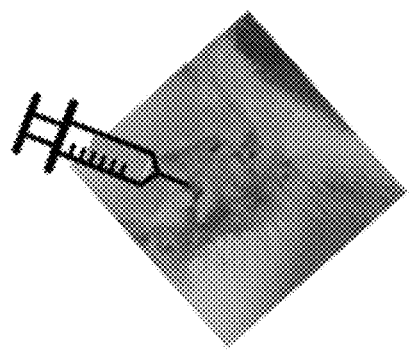
Figure 5A:
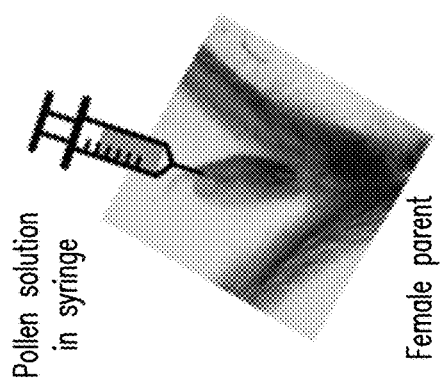

In particular embodiments, the pollen solution can be introduced into a flower bud of a recipient plant by injecting the solution into the bud such that solution makes contact with the stigma. The injecting may be carried out using any instrument having the capacity to inject a desired amount of solution in the flower bud without disrupting the stigma and ovule. A non-limiting example is a syringe (FIG. 5A).

In some embodiments, the flower bud can be modified to facilitate cross-pollination using the solution containing donor pollen. In certain aspects, a portion of the tip of the flower bud may be removed by cutting, thereby creating an opening for the pollen solution to make contact with the stigma while keeping the flower bud mostly intact (FIGS. 5B and 5C).

In further embodiments, the methods of the present invention may comprise selecting a progeny seed or plant that results from said pollinating with the pollen solution. This could be facilitated by use of a polymorphic marker allele contained in the pollen donor that serves to identify progeny plants or seeds of that donor. Morphological markers or biochemical/protein markers have commonly been used as tools for selection of plants with desired traits in breeding. The molecular marker techniques that have been extensively used and are particularly promising for application to plant breeding include: restriction fragment length polymorphisms (RFLPs), amplified fragment length polymorphisms (AFLPs), random amplified polymorphic DNA (RAPD), microsatellites or simple sequence repeats (SSRs), and single nucleotide polymorphisms (SNPs) (Al-Khayri et al., 2016).

In still other embodiments, the methods described herein may comprise pollination of flowers that are male sterile at the time of pollinating. Given that the stigma is not exposed in soybean flowers and depending upon the developmental stage of the flower, for example, donor pollen applied for cross-pollination could compete with pollen produced by the recipient plant. In order to improve the efficacy of the cross-pollination, it may be advantageous in some cases that the flowers on the recipient plant be male sterile in an effort to reduce competition with selfing. Thus, a male sterility system could be employed with the female (flower) parent plant in a particular cross. Many such male sterility systems are well known, including cytoplasmic male sterility (CMS) and genic male sterility (GMS). CMS and GMS facilitate hybrid seed production for many crops and thus allow breeders to harness yield gains associated with hybrid vigor (heterosis). Eleven male-sterile, female-fertile mutants (ms1, ms2, ms3, ms4, ms5, ms6, ms7, ms8, ms9, msMOS, and msp) have been identified in soybean (Graybosch and Palmer, 1988). The use of a gametocide presents an alternative method to produce male sterility. Several gametocides have been reported effective in inducing pollen sterility in various crops and are well known in the art. Such gametocides include sodium methyl arsenate, 2,3-dichloroisobutyrate, sodium 2,2-dichloropropionate, gibberellic acid, maleic hydrazide (1,2-dihydropyridazine, 3-6-dione), 2,4-dichloro phenoxy acetic acid, ethyl 4-fluorooxanilate, trihalogenated methylsulfonamides, ethyl and methyl arsenates (Ali et al., 1999).

In some embodiments, the step of introducing the pollen solution to the enclosed stigmas of flower buds of the recipient plant can be performed at a rate of about 10 seconds per flower bud. In other embodiments, the pollinating is defined as taking less than about 20 seconds, 30 seconds, 40 seconds or 60 second per flower on average. This is significantly faster than traditional pollination methods, which may take up to 5 minutes per flower. Thus, the disclosed methods can be about 20-30 times faster than traditional methods. The highly efficient methods of the invention are therefore amenable to implementation in a high-throughput system. One aspect of the invention therefore comprises contemporaneously carrying out the methods of the invention on a plurality of plants. In certain aspects, the plurality of plants comprises at least about 10, 50 100, 250, 500, 1,000, 5, 000, 10,000, 50,000, or 100,000 or more plants. The methods may be carried out in a field or in a controlled growth environment such as a greenhouse or growth chamber.

The methods disclosed herein may be implemented for improved cross-pollination of potentially any plants that have a female recipient flower where the stigma is still enclosed by flower structures such as petals and sepals at the time of crossing. Such plants may include, but are not limited to, soybean, barley, wheat, rice, lettuce, chickpea, peanut, eggplant, pepper and tomato.

Modified Plants and Seeds

One aspect of the invention provides selection of progeny plants and seeds that result from the methods described herein. In some embodiments, the progeny plants and seeds may be defined as comprising a detectable modification relative to the flower parent plant. One method of producing such plants and seeds is through use of an allele produced by plant genetic transformation. Suitable methods for transformation of host plant cells for use with the current invention are well known in the art and include any method by which DNA can be introduced into a cell (for example, where a recombinant DNA construct is stably integrated into a plant chromosome) and are well known in the art. Some widely utilized methods for cell transformation are *Agrobacterium*-mediated transformation, microprojectile bombardment-mediated transformation, and cell penetrating peptide-mediated delivery of DNA modifying agents.

Another method of producing modified plants and seeds is through genome editing. As used herein, the term "genome editing" refers to the use of genome editing methods and a site-specific genome modification enzyme to modify a nucleotide sequence. In some embodiments, donor pollen purified by the methods provided herein may be transformed using techniques known in the art to contain one or more reagents that mediate genome-specific modification in a plant. Pollen grains may be used in accordance with the invention that comprise any such reagents of loci generated with use of such reagents at any current or prior generation.

Suitable methods for altering a wild-type DNA sequence at a pre-determined chromosomal site include any method known in the art. Targeted modification of plant genomes through the use of genome editing methods and reagents can be used to create improved plant lines through modification of plant genomic DNA. In addition, genome editing methods and reagents can facilitate targeted insertion of one or more nucleic acids of interest into a plant genome. Exemplary methods for introducing donor polynucleotides into a plant genome or modifying the genomic DNA of a plant include the use of genome editing reagents such as: sequence-specific recombinases, endonucleases, zinc-finger nucleases, engineered or native meganucleases, TALE-endonucleases, RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system), and CRISPR-associated transposases ((Strecker et al., 2019) and (Klompe et al. 2019). Several embodiments relate to methods of genome editing using single-stranded oligonucleotides to introduce precise base pair modifications in a plant genome, as described by Sauer et al. (*Plant Physiol.* 170 (4):1917-1928; 2016).

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

EXAMPLES

Figure 2:
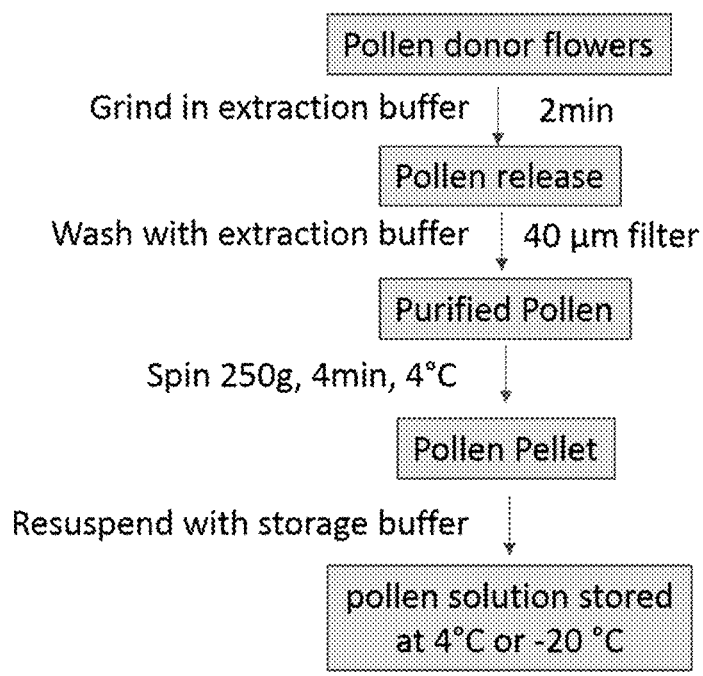
FIG. 2: Shows a diagram of the steps in pollen solution preparation, including pollen grain collection, purification, and storage. Different storage buffers can be used based on the respective extraction buffer used. For example, if 20% sucrose is used as the extraction buffer, the purified pollen will be stored in 80% sucrose at 4° C. If oil is used as the extraction buffer, the purified pollen will be stored in oil at −20° C.

Example 1. Improved Methods for Collection, Purification, and Storage of Pollen In some plants, especially soybean, it is difficult to collect pollen due to the size and structure of the flowers. In addition, soybean pollen grains are relatively small in size (about 26 μm) and are present in relatively small quantities in a single flower (approximately 3000 to 7000 pollen grains/flower) (Palmer et. al., 1978). To meet the needs for large-scale pollination using the methods described herein, a liquid-based platform may be developed to optimize the collection, purification, and storage of donor pollen. This includes the steps of disruption of collected flowers (for example, by grinding or by homogenizing with or without liquid using a bead mill homogenizer) to release pollen, filtration of the disrupted flowers to purify the released pollen, collection of the purified pollen by centrifugation, and resuspension of the purified pollen a solution that is suitable for storage or for use in liquid pollination (FIG. 2). The purified pollen may be stored in an 80% sucrose solution at 4° C., in corn oil at −20° C., or any other suitable storage solutions for later use.

Purified pollen may be quantified using a hemocytometer to determine the number of pollen grains obtained from the purification process. Quantification of the pollen enables production of pollen solutions containing a desired density of pollen and to ensure that a fixed amount is consistently administered, which reduces the likelihood of large amounts of variation in the results obtained from efficiency assays that test different pollen solutions and further decreases the influence of debris on pollination efficiency. This simple and fast method may be used for any other species to collect and store purified pollen.

Example 2. Development of Solution for Delivery of Pollen

For liquid pollination of plants, pollen grains obtained from a donor plant can be mixed into a liquid solution to facilitate delivery into the flower bud. The components and their concentrations in the pollen liquid solution are important to the efficacy of the solution, as they influence not only the pollen viability itself but also the success rate of hybrid seed set in pollinated plants. However, while efficiency can be improved by optimization of the components and concentration in a given pollen solution, numerous substitutions and modifications are possible while still achieving pollination as illustrated herein below in Table 1.

TABLE 1

Measures of pod-set success rate when pollinating using various pollen solutions

| Pollen Solution | Pod-set Success Rate |
| --- | --- |
| Conventional cross-pollination | 60% |
| 5% sucrose | 0% |
| 10% sucrose | 29% |
| 15% sucrose | 18% |
| 20% sucrose | 33% |
| 25% sucrose | 0% |
| 20% sucrose, 0.04% xanthan gum, 0.01% Tween 20 | 40% |
| 20% sucrose, 0.04% xanthan gum, 0.05 U/L PG | 22% |
| 20% sucrose, 0.04% xanthan gum, 0.5 U/L PG | 11% |
| 20% sucrose, 0.04% xanthan gum, 5 U/L PG | 0% |
| 20% sucrose, 0.04% xanthan gum, 50 U/L PG | 0% |
| 20% sucrose, 0.04% xanthan gum, 1500 U/L PME | 14% |
| 20% sucrose, 0.04% xanthan gum, 150 U/L PME | 11% |
| 20% sucrose, 0.04% xanthan gum, 1.5 U/L PME | 29% |
| 20% sucrose, 0.04% xanthan gum, 15 U/L PME | 56% |
| 20% sucrose, 0.04% xanthan gum, 0.001% Tween 20, 0.02% MgSO$_4$, 0.02% ZnSO$_4$ | 20% |
| 20% sucrose, 0.04% xanthan gum, 0.01% boric acid, 0.001% Silwet L-77, 0.02% MgSO$_4$, 0.02% ZnSO$_4$ | 43% |
| 20% sucrose, 0.04% xanthan gum, 0.01% boric acid, 0.001% Pluronic, 0.02% MgSO$_4$, 0.02% ZnSO$_4$ | 45% |
| 20% sucrose, 0.04% xanthan gum, 0.01% boric acid, 0.001% Tween 20, 0.02% MgSO$_4$, 0.02% ZnSO$_4$ | 52% |
| 20% sucrose, 0.04% xanthan gum, 15 U/L PME, 0.001% Tween 20, 0.02% MgSO$_4$ | 50% |
| 20% sucrose, 0.04% xanthan gum, 15 U/L PME, 0.001% Tween 20, 0.01% BSA, 0.02% MgSO$_4$, 0.02% ZnSO$_4$ | 64% |

Figure 3:
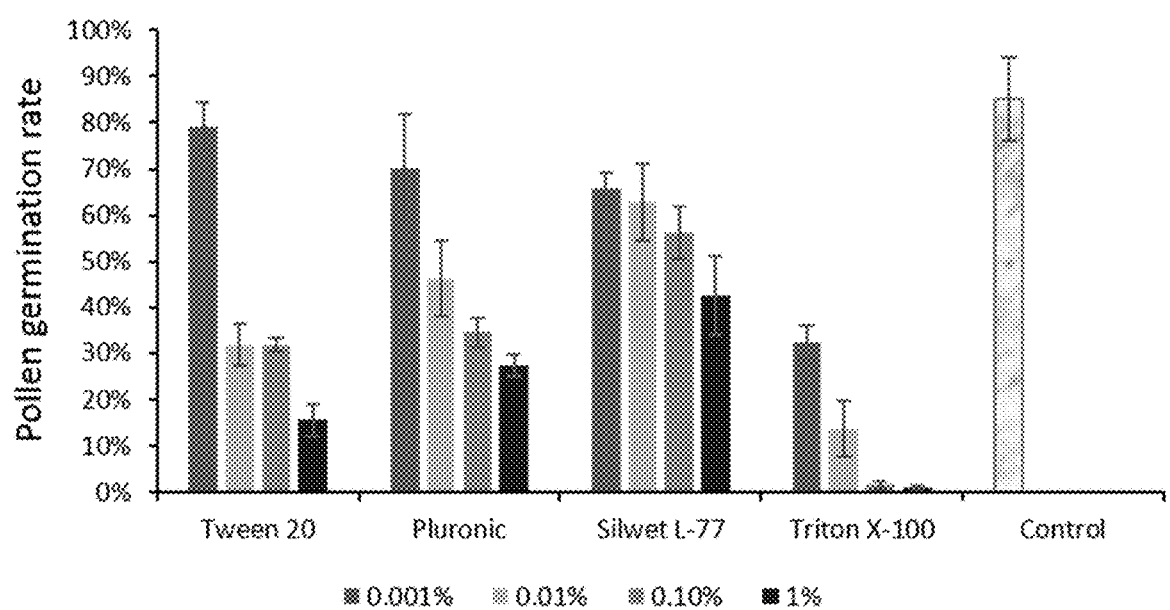
FIG. 3: Shows the impact of surfactants on in vitro pollen germination rate. Pollen grains were added to a pollen germination medium (GM: 20% sucrose, 0.03% calcium nitrate, 0.01% boric acid) containing a different surfactant at the concentrations as indicated. The control was pollen germination without surfactant. After incubation for 2 hours at 25° C., germination rates were recorded (mean SE; n=3 replicates, 100-150 pollen grains for each replicate). The pollen grain is considered germinated when the length of its tube is more than the diameter of the pollen grain.

To lower the surface tension between pollen liquid solution and plant tissue, a test was performed to identify a suitable surfactant that would not disturb pollen tube growth and help delivery of pollen liquid solution to stigma. Different surfactants, including Tween 20, Pluronic, Silwet L-77, and Triton X-100 were tested with dose titration. Germination buffer containing 0.001% Tween 20 showed pollen germination rates comparable to the control (FIG. 3A). Tween 20, Pluronic, and Silwet L-77 were selected for the initial liquid pollination test and used at a concentration of 0.001% (Table 1, above).

Figure 4:
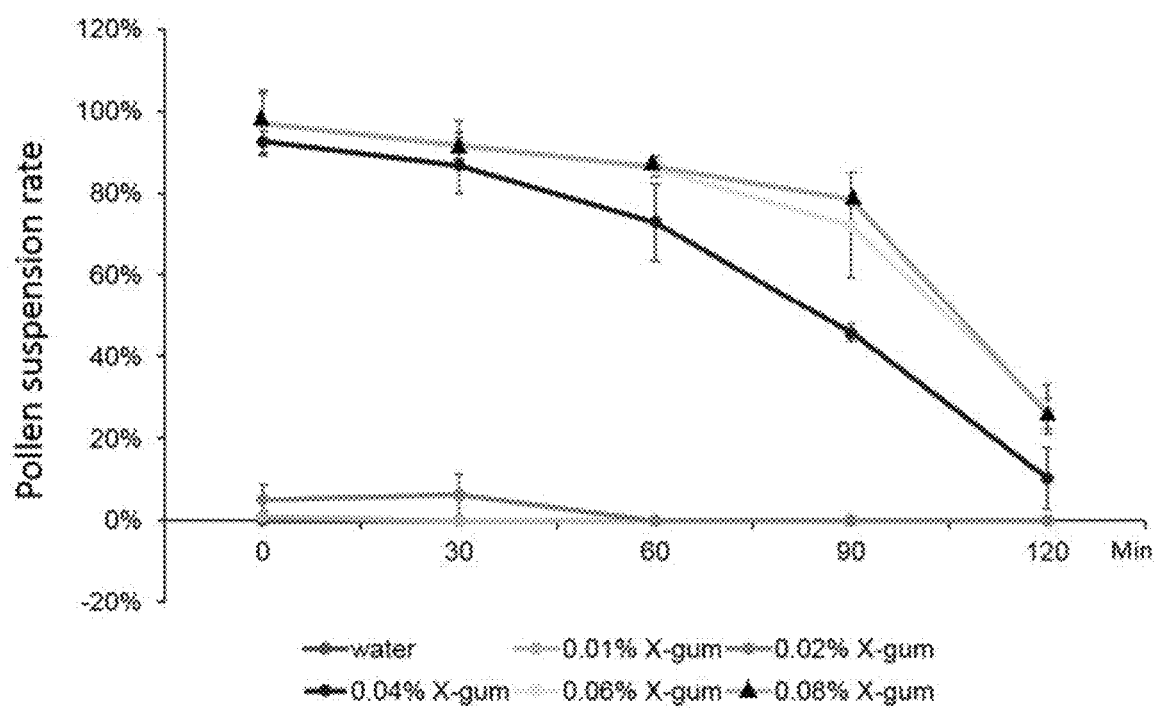
FIG. 4: Shows the measurement of pollen uniformity in suspensions containing different concentrations of xanthan gum. Collection time points are shown on the x-axis (in minutes) and pollen suspension rate (collection from top of solution/collection from bottom of solution) is shown on the y-axis (mean SE; n=3).

The use of xanthan gum was also tested in the liquid solution to improve the dispersion of pollen in the solution. This test as performed by adding pollen to a tube containing a solution containing 0.01% to 0.08% xanthan gum and each pollen solution was left undisturbed after mixing. 20 μl samples of the pollen suspension were taken from the top and bottom portions of the tube at time points of 0, 30, 60, and 90 minutes post mixing, and placed on a slide. The number of pollen grains was counted, and the process was repeated three times to derive pollen suspension rate (the ratio of pollen count from solution collected from the top of the tube to the pollen count from solution collected from the bottom of the tube), indicating the distribution level of the pollen in suspension (FIG. 4). Xanthan gum used at concentrations of 0.4%-0.8% appeared to be an optimal range for the pollen suspension in this study.

Sucrose is used as a major regulator of osmotic pressure. If the concentration is too high or too low, it will destroy the osmotic balance and result in loss of viability of the pollen in solution. The effects of sucrose concentration on liquid pollination were tested (Table 1, above). It was observed that 10%-20% sucrose in the tested pollen liquid solutions yielded positive results.

A pectinase can be used to help improve pollination success of pollen in the liquid solution. Such pectinases may include pectin methylesterase (PME) or polygalacturonase (PG). An experiment was carried out to determine the pod-set success rates using pollen in liquid solutions containing varying concentrations of PG or PME. Each pollen solution was tested in three independent trials using 15-20 samples per trial. When pollen grains were suspended in medium containing PG at concentrations ranging from 0.005 U/L-5 U/L, the pod set success rates were not significantly different from those of the controls. Media supplemented with PME at concentrations of 1.5 U/L, 150 U/L, and 1500 U/L also showed no significant effect on pollination, but media supplemented with PME at a concentration of 15 U/L resulted in a higher pod set success rate than the control (0 U/L PME in 20% sucrose, 0.04% xanthan gum solution). The results are shown in Table 1, above. The addition of 15 U/L of PME increased the percentage of pod set, making the success rate comparable to conventional cross-pollination techniques.

Additional components may be utilized in the pollen liquid solution described herein. BSA (0.1 mg/ml) may be used as a carrier protein in a solution comprising a pectinase to protect against enzyme activity loss. $MgSO_4$ (0.01%-0.05%) is believed to support $Ca^{2+}$ uptake or binding. $ZnSO_4$ is believed to protect the pollen tube against free radicals during pollen tube growth. Boron is thought to be directly involved in membrane pectin synthesis in relation to pollen tube growth. It was observed that the addition of boric acid, along with $MgSO_4$ and $ZnSO_4$, in the pollen liquid solution improved the success rate of liquid pollination. When adding both $MgSO_4$ and $ZnSO_4$ with PME in the liquid pollination solution, the success rate reached 64%, which is comparable to the success rate using conventional cross-pollination techniques (Table 1, above).

Example 3. Liquid-Mediated Pollen Delivery in Soybean Plants

Figure 5D:
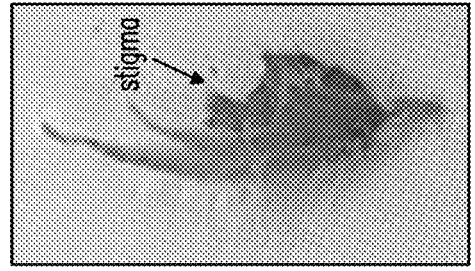
Figure 5D:
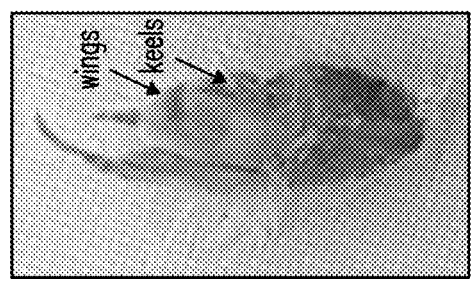
Figure 5D:
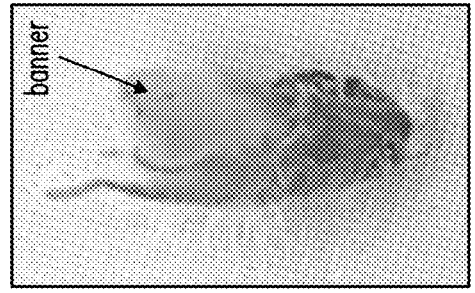
Figure 5D:
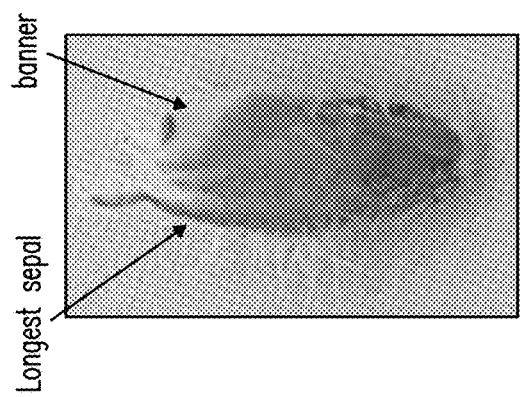

A suitable liquid-mediated pollen delivery method was evaluated by a dye inspection method using soybean flower buds. Injection buffer (20% sucrose, 0.04% xanthan gum, 15 U/L PME, 0.001% Tween 20 and Allura Red AC 0.01%) was delivered into hooded flower buds by inserting a syringe needle at the bending point of longest sepal and injecting the buffer until excess liquid oozed out. Five minutes after injection, the flower buds were dissected to inspect the red stain on the stigma. The red stain on the stigma indicates that the administered liquid successfully made contact with the stigma (FIG. 5D).

Based on the results obtained from experiments testing the individual components, it was determined that beneficial components for a solution for pollen delivery in soybean include, but are not limited to, the following components: xanthan gum: 0.04%-0.08% (w/v); sucrose: 10-20% (w/v); PME: 0.01-10 mg/L; and Tween 20: 0.001%-0.01% (v/v). The liquid solution may also include BSA (0.1 mg/ml) to stabilize the PME; and mineral ions, such as $MgSO_4$ (0.01%-0.05%) to support $Ca^{2+}$ uptake or binding; $ZnSO_4$ (0.01%-0.05%) to promote pollen germination and pollen tube growth; and boric acid (0.005%-0.02%) to regulate pollen germination and pollen tube growth. These and other components can be optimized for a given application.

Figure 6A:
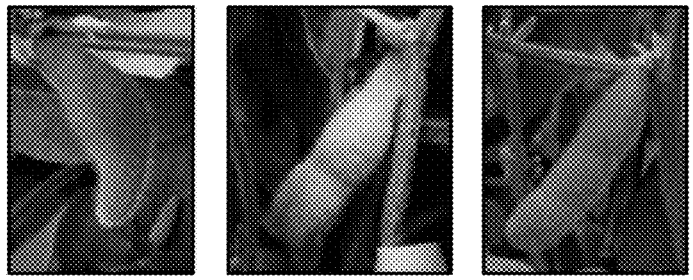
FIGS. 6A, 6B, 6C, and 6D: Show images of representative seed sets from different pollination techniques.
Figure 6B:

To analyze this, pollen solutions comprising combinations of the components at various concentrations were prepared for liquid pollination. Bright opened flowers from male donor plants were selected for pollen collection. Pollen was collected following the methods described in Example 1 above. The purified pollen was resuspended in different liquid pollination solutions (Table 1, above). Unopened buds on a male-sterile female parent were selected for pollination. The pollen solutions were delivered to enclosed stigmas of recipient flowers by injecting a volume of 2-5 μl of pollen solution to each unopened flower buds. Liquid-mediated pollination and control (conventional pollination) groups were compared for percentage of pollinations that produced a pod (percent success). 15 days after pollination, pod-setting was measured. The pod-setting rate varied from 7% to 64% in liquid-mediated pollination treatments relative to 60% for the control (Table 1, above). The representative pod-setting images are shown in FIGS. 6A and 6B.

Example 4. Production of Hybrid Plants and Confirmation of Hybridity

A study was performed to determine if production of outcrossed progeny could be optimized by rendering plants male sterile using gametocide without impacting female fertility. In this study, maleic hydrazide (at 50, 150, and 250 ppm) or distilled water was sprayed once at the time of flower primordia initiation on the stems of plants of the male fertile line. Care was taken to ensure that all the plants were evenly sprayed. Male sterile plants were produced and had a very similar phenotype (producing pods without seeds) to plants of the ms6 male-sterile line derived from soybean variety 01046197 (FIG. 7B). Soybean variety 01046197 is disclosed in U.S. Pat. No. 9,232,755, the entire content of which is incorporated by reference herein. Female fertility was not impacted by maleic hydrazide treatment and flower buds developed into seed-bearing pods when cross-pollinated (FIG. 7C), which appeared similar to the seed-bearing pods produced by untreated controls (FIG. 7A). Therefore, gametocide-induced male-sterility can be used to improve cross-pollination efficiency using pollen in a liquid solution.

Figure 6C:
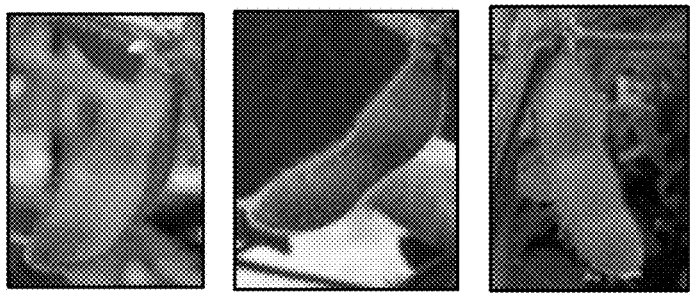
Figure 6D:
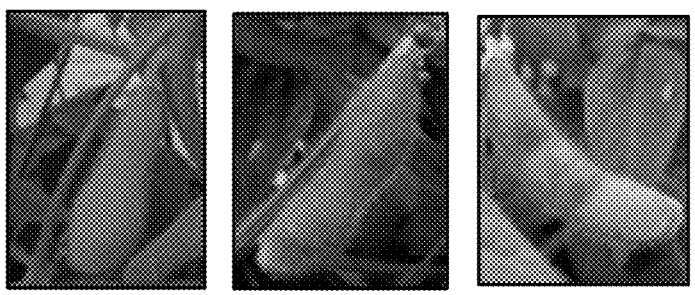

A study was also performed to determine whether liquid-mediated delivery of pollen grains from donor plants can compete with self-pollinations in a recipient plant. A "self-fertile" plant as used herein is a plant that successfully sets seed when self-pollinated (i.e. by its own pollen). In this study, a line that is self-fertile was selected as the female recipient plant. A liquid solution containing pollen from a donor line comprising a dominant phenotypic marker (purple hypocotyl) was applied to a self-fertile female recipient line bearing a recessive phenotypic marker (lightgreen hypocotyl). If the cross pollination is successful, one would expect to see the progeny to have a purple hypocotyl, as this color trait is contributed by the male parent. Progeny plants having purple hypocotyls were observed (not shown), indicating that liquid-mediated pollination of a self-fertile recipient parent was able to produce hybrid offspring from donor pollen delivered in the liquid solution. Representative seed set is shown in FIGS. 6C and 6D.

In addition, the resultant progeny plants were tested for hybridity based on genotyping using molecular markers on multiple chromosomes. The presence of various polymorphisms in the genome can be widely used as genetic markers. Many DNA genotyping methods utilize these genetic markers to differentiate various plant lines and to study the evolutionary relationships between them. SNP genotyping assays provide a highly flexible technology for detection of polymorphisms within any genome.

A TaqMan SNP genotyping assay was used with eight selected markers (SEQ ID NOs:1-8) for the genotyping of hybrid progeny plants. The genotyping results are shown in Table 2 below. Four out of seven progeny plants were hybrids resulting from liquid-mediated delivery of pollen to a self-fertile recipient line.

The SNP at nucleotide position 201 of molecular marker SEQ ID NO: 1 can be detected with probes indicated as SEQ ID NO: 25 (Probe 1) and SEQ ID NO: 33 (Probe 2) using a TaqMan assay. One of skill in the art will recognize that sequences to either side of the given primers can be used in place of the given primers, so long as the primers can amplify a region that includes the allele to be detected. The precise probe used for detection can vary, e.g., any probe that can identify the region of a marker amplicon to be detected can be substituted for those probes exemplified herein. Configuration of the amplification primers and detection probes can also be varied. Thus, the invention is not limited to the primers, probes, or marker sequences specifically recited herein.

Novel methods for liquid-based pollen collection, purification, and delivery of pollen grains for soybean pollination and optimized liquid solutions suitable for liquid-mediated pollination in soybean are provided herein. As described above, hybrid plants were successfully produced and hybridity was confirmed using phenotypic and genotypic assays. These results showed that it is possible to deliver donor pollen in a liquid solution to enclosed stigmas of recipient flowers and that pollen delivered in such a manner can

TABLE 2

Confirmation of hybrid plants using molecular markers

| | MARKERS | | | | | | | |
|---|---|---|---|---|---|---|---|---|
| | SEQ ID NO: 1 | SEQ ID NO: 2 | SEQ ID NO: 3 | SEQ ID NO: 4 | SEQ ID NO: 5 | SQ ID NO: 6 | SEQ ID NO: 7 | SEQ ID NO: 8 |
| Chromosome | 1 | 2 | 3 | 4 | 6 | 8 | 9 | 11 |
| Position (cM)* | 39 | 96.7 | 218 | 188 | 150 | 165 | 45.3 | 64.8 |
| Pollen donor line | AA | TT | AA | CC | GG | GG | CC | GG |
| Male-fertile recipient line | GG | CC | GG | TT | AA | CC | TT | AA |
| Hybrid (expected genotype) | AG | CT | AG | CT | AG | CG | CT | AG |
| Sample 1 | GG | CC | GG | TT | AA | CC | TT | AA |
| Sample 2 | AG | CT | AG | CT | AG | CG | CT | AG |
| Sample 3 | GG | CC | GG | TT | AA | CC | TT | AA |
| Sample 4 | AG | CT | AG | CT | AG | CG | CT | AG |
| Sample 5 | GG | CC | GG | TT | AA | CC | TT | AA |
| Sample 6 | AG | CT | AG | CT | AG | CG | CT | AG |
| Sample 7 | AG | CT | AG | CT | AG | CG | CT | AG |

"*"cM = centiMorgans on the Monsanto internal soybean genetic map

The primer sequences for amplifying exemplary molecular marker loci and the probes used to genotype the corresponding molecular marker sequences are provided in Table 3 below.

TABLE 3

Exemplary primers and probes used for genotyping representative molecular markers

| Marker (SEQ ID NO) | SNP Position | Forward Primer (SEQ ID NO) | Reverse Primer (SEQ ID NO) | Probe 1 (SEQ ID NO) | Probe 2 (SEQ ID NO) |
|---|---|---|---|---|---|
| 1 | 201 | 9 | 17 | 25 | 33 |
| 2 | 201 | 10 | 18 | 26 | 34 |
| 3 | 549 | 11 | 19 | 27 | 35 |
| 4 | 201 | 12 | 20 | 28 | 36 |
| 5 | 280 | 13 | 21 | 29 | 37 |
| 6 | 201 | 14 | 22 | 30 | 38 |
| 7 | 201 | 15 | 23 | 31 | 39 |
| 8 | 201 | 16 | 24 | 32 | 40 |

In an illustrative example, marker SEQ ID NO: 1 can be amplified using the primers SEQ ID NO: 9 (forward primer) and SEQ ID NO: 17 (reverse primer) as shown in Table 3.

compete with self-pollination to produce seeds in soybean. The methods described herein aim to enable liquid-mediated delivery of pollen grains to enclosed stigmas of recipient flowers and to achieve a low cost and high efficiency pollination system in soybean. The methods described herein can be further enhanced by developing a device for automated administration of pollen solutions and/or utilizing imaging identification technology to select optimal flower buds.

In some embodiments, imaging systems can be used to determine flower stage and injection angle. In other embodiments, digital pipettes can be used to administer a desired volume of the liquid pollination solution. In some embodiments, robotic systems such as robotic arms or robotic bees (Wood et al., 2013) can be used to automate the liquid-mediated pollen delivery process. For example, a robotic bee may be equipped with an image recognition system to detect suitable recipient flowers for cross pollination. A robotic bee may also be equipped to carry a cartridge loaded with liquid pollen solution. Once a suitable recipient flower is identified, the robotic bee can inject a suitable volume of liquid pollen solution into the recipient flower to enable cross pollination.

Example 5. Further Applications of the Novel Liquid-Mediated Pollination Platform Transgenic seeds or gene-edited seeds of recipient plants may be directly generated through liquid-mediated pollination with exogenous DNA-transformed pollen. Collected pollen may be transformed through physical methods such as electroporation, bombardment and sonication, *Agrobacterium* infection, pollen tube-mediated transfection, or magnetofection (Zhao et al., 2017). For example, CRISPR/Cpf1 reagents may be delivered into purified pollen grains using electroporation or magnetofection. The transformed pollen is then selected and placed into the liquid solutions provided herein. The pollen solution may then be injected into flower buds to create genome-edited seeds. It is feasible to utilize the liquid-mediated pollination system provided herein and CRISPR/Cpf1-based gene editing for trait discovery and improvement in plants. This combination obviates the need for the laborious steps of tissue culture while producing transgenic or gene-edited plants from transformed seeds within a short period of time.

The present invention provides a tissue culture-independent plant transformation method, which can be used to deliver pollen solution containing 0.05% surfactant Silwet L-77 and *Agrobacterium tumefaciens* comprising genes for trait improvement into flower buds for the transformation of soybean. The optimal stage of floral development will be targeted by repeat inoculations on different days to ensure maximum access of *Agrobacterium* for increasing transformation rate.

The methods provided herein could also be utilized to deliver exogenous DNA to recipient plants for plant pathogen-free transformation-gene editing. Previous studies have reported that exogenous DNA can be introduced into plants via the pollen-tube pathway or ovary-drip transformation (Yang et al., 2009). These methods have been used in several crops, including cotton, rice, and soybean. The present invention provides a means to combine liquid pollination with exogenous DNA, by administering a DNA solution comprising desired exogenous DNA with a pollen solution as described herein, for the transformation of zygotic cells without normal cell walls. By combining the solutions, the exogenous DNA could reach the ovary by flowing down the pollen tube and integrate into zygotic cells that have been fertilized but are still undivided. The transformed seeds could be obtained directly without protoplast preparation, cell culture, and plant regeneration.

The invention claimed is:

1. A method for liquid-mediated delivery of pollen to an enclosed stigma of a flower from a recipient soybean plant comprising the steps of:
   a) obtaining pollen from a donor soybean plant;
   b) producing a liquid solution comprising said pollen; and
   c) injecting said solution into an enclosed stigma of an unopened flower bud on a recipient soybean plant, thereby pollinating the flower bud with the pollen from the donor soybean plant, wherein the enclosed stigma is enclosed by flower structures.

2. The method of claim 1, wherein said pollen is obtained from a plurality of flowers from said donor soybean plant.

3. The method of claim 1, further comprising the step of selecting a progeny seed or plant that results from said pollinating.

4. The method of claim 3, wherein the donor soybean plant comprises an allele that facilitates selecting said progeny plant or seed.

5. The method of claim 1, wherein the flower bud is male sterile at the time of said pollinating.

6. The method of claim 5, wherein the recipient soybean plant is genetically male sterile or wherein the flower bud or recipient soybean plant is treated with a gametocide.

7. The method of claim 1, wherein said solution comprises at least a first component selected from the group consisting of a pectinase, a thickening agent, a surfactant, sucrose, a plant growth regulator, a mineral ion, a carrier protein, and a nucleic acid molecule.

8. The method of claim 7, wherein said solution comprises said pectinase and wherein said pectinase is a pectin methylesterase.

9. The method of claim 7, wherein said solution comprises
   (a) pectin methylesterase at a concentration of about 1.5 units/L to about 1500 units/L;
   (b) about 0.04% to about 0.08% xanthan gum by weight;
   (c) about 0.001% to about 0.01% Tween 20 by weight;
   (d) about 10% to about 20% sucrose by weight;
   (e) about 0.01% to about 0.05% $MgSO_4$ by weight;
   (f) about 0.01% to about 0.05% $ZnSO_4$ by weight;
   (g) about 0.005% to about 0.02% boric acid by weight; or
   (h) about 0.01% to about 0.1% bovine serum albumin (BSA) by weigh.

10. The method of claim 7,
   (a) wherein said solution comprises said thickening agent, wherein said thickening agent comprises xanthan gum;
   (b) wherein said solution comprises said surfactant, wherein said surfactant comprises Tween 20; or
   (c) wherein said solution comprises said carrier protein, wherein said carrier protein comprises bovine serum albumin (BSA).

11. The method of claim 7, wherein said solution comprises said mineral ion and wherein said mineral ion is selected from the group consisting of $MgSO_4$, $ZnSO_4$, and boric acid.

12. The method of claim 1, further comprising collecting seed resulting from said pollinating.

13. The method of claim 12, comprising crossing a progeny plant grown from said seed with itself or a second plant.

14. A method of producing hybrid seed comprising the steps of:
   a) obtaining pollen from a soybean donor plant;
   b) producing a liquid solution comprising said pollen;
   c) injecting said solution into an unopened flower bud of a female soybean parent having a genotype that is different from that of the soybean donor plant, wherein the flower bud comprises an enclosed stigma that is enclosed by flower structures, thereby pollinating the flower with pollen from the soybean donor plant;
   d) harvesting seed produced from said pollination; and
   e) identifying hybrid progeny.

15. The method of claim 14, wherein the donor plant is a soybean plant.

16. A method of producing an $F_1$ hybrid soybean seed comprising the steps of:
   a) preparing a pollen suspension solution comprising a desired pollen concentration from a donor soybean plant;
   b) introducing said pollen suspension solution to an enclosed stigma of an unopened flower bud of a female soybean parent having a genotype that is different from that of the donor plant, wherein the enclosed stigma is enclosed by flower structures, wherein said pollen suspension solution is introduced to the stigma by injecting said solution into the enclosed stigma, thereby pollinating the flower with pollen from the donor plant; and
   c) harvesting $F_1$ seed produced from said pollination.

17. The method of claim 16, wherein said solution comprises at least a first component selected from the group consisting of a pectinase, a thickening agent, a surfactant, sucrose, a plant growth regulator, a mineral ion, a carrier protein, and a nucleic acid molecule.

18. The method of claim 16, wherein the flower bud of the female soybean parent is male sterile.

19. The method of claim 16, further comprising identifying the $F_1$ hybrid seed using phenotypic or genotypic markers.

20. The method of claim 1, wherein the flower structures comprise petals and sepals.

21. The method of claim 14, wherein the flower structures comprise petals and sepals.

* * * * *

SEQUENCE LISTING

```
<160> NUMBER OF SEQ ID NOS: 40

<210> SEQ ID NO 1
<211> LENGTH: 301
<212> TYPE: DNA
<213> ORGANISM: Glycine max
<220> FEATURE:
<221> NAME/KEY: misc_feature
<222> LOCATION: (80)..(80)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t

<400> SEQUENCE: 1
tactagtcga atgagtcggt aacaaatagg atcacaaatt taaggtttaa acctactcaa      60
caaatcatcc taatcccatn tgtnccatac tcggagagtt tacacacatg gggcctacca     120
tgtaattgga gggaagatgt aaagcgatta ccaagttggt agctatcctc aattgggtca     180
ttcatgccat atgtttaagg nagatacaag gtaagtaatc taacatgttt atcacttcgg     240
attaaactaa cttgagcgtt agaatctcaa tgtaagtatc tcaccattca ttagagagga     300
t                                                                    301

<210> SEQ ID NO 2
<211> LENGTH: 301
<212> TYPE: DNA
```

```
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 2
aattctaaat ttctataaaa gcaatttcac tgatcatgtg atactagcta agaagcaatt      60
gccattattt agaaatagat agagaagggg gaggggaaca gtgattatta atgttcagta     120
accttatcat gcaagcaaac taccaattta tgctgtgtta atgtttctat tgagccgtgc     180
ccttctctag ttatatttga nacatcagtg ttccatcata aatattatca tctcaccatc     240
tactctgaag ctactaggaa gattgagttc aatcttcaca aaaatatatt aagacaatgt     300
c                                                                    301

<210> SEQ ID NO 3
<211> LENGTH: 886
<212> TYPE: DNA
<213> ORGANISM: Glycine max
<220> FEATURE:
<221> NAME/KEY: misc_feature
<222> LOCATION: (549)..(549)
<223> OTHER INFORMATION: n is a, c, g, or t

<400> SEQUENCE: 3
tccaactgaa atccaaacat gctaaagatg gttgtacttg ctttagaact taatattagt      60
actgacaatg tgacttgctt gatagtcttc tttagtttat tgcacttata acctacttaa     120
catctatatg taacattgga gttaaatcat gcttggtata tgatttattt gaaaaaaaaa     180
atggacagga tggggtgcag gtttactttc cccaagcaat tagcaaaaca tgtagggaga     240
ggggccaggt tgcccctatg ttgttggagt tgggtgtcta tttctataac ctacgtgcta     300
atataatgca acaatgagt agtgaaagac tacgaaccat tttctagttt cattgaactt     360
atcatatgga caatgtaatc catattaaac tcatgctgtt actgttatta ttctactcaa     420
ttgataattc ttgtatatat tttctgtatc tgttcagttc ttgatattat gattttgtga     480
tagcctgatg tgtaatattt tacatttatc atctttccta gggaggcgtt ctttctggtg     540
tgagtgtgnc attactagtt tcctgataga agaaagtcta atggcacatt caacaagctt     600
gatctttatg ggccgcagtt ttagtccact tcctaaaacc aaagtcagtg tatctggaag     660
gcttgtctcc agatcttcag caggacttcg cattcaagct gtgcaagaga acggtggacc     720
acgaagacta gtggacatta ttagacttgt gcctgagctc tcaaggaatt aattacttta     780
gaagccattc tcacagggct ctgtttggtg gaatctcatt gttgggtgga ttttatgtgg     840
cacaaacaat ctctcttttg gagctctagg agtcaatgat gttatt                   886

<210> SEQ ID NO 4
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 4
cccttgcgct caacctatta tatcaaataa aaaaacataa agtttaattg tacatatagt      60
gaacaagaca aggccaaggt ttgaacagtg gtaaatacc tacctttatc ccatgaatct     120
gaattttccc aattttcgga aagcataagg gatgttccga cagaatactc tctacataaa     180
```

```
gaaatgcatt taaagttaaa naaaaggtca tcactattaa gaacatagaa ccaaaaccga    240
tatactaaga acaaaaactg ttaacaagaa gatgaaagaa ggatctgcat gaactataaa    300
a                                                                    301

<210> SEQ ID NO 5
<211> LENGTH: 301
<212> TYPE: DNA
<213> ORGANISM: Glycine max
<220> FEATURE:
<221> NAME/KEY: misc_feature
<222> LOCATION: (280)..(280)
<223> OTHER INFORMATION: n is a, c, g, or t

<400> SEQUENCE: 5
cccttgcgct caacctatta tatcaaataa aaaaacataa agtttaattg tacatatagt     60
gaacaagaca aggccaaggt ttgaacagtg gtaaatacc taccttttatc ccatgaatct    120 gaattttccc aattttcgga aagcataagg gatgttccga cagaatactc tctacataaa    180
gaaatgcatt taaagttaaa taaaaggtca tcactattaa gaacatagaa ccaaaaccga    240
tatactaaga acaaaaactg ttaacaagaa gatgaaagan ggatctgcat gaactataaa    300
a                                                                    301

<210> SEQ ID NO 6
<211> LENGTH: 866
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 6
cagccgaatg caatccaaca gcggtgaaac ttcacctcca tttatgaaat cttccagaaa     60
ctgtacagaa tagaagcatc taatttagta aatacatagg gaggaattta tcttgggaac    120
agatccagga caaatatta gatacatcta tacaaaagac aacttaaaat taaggaattg    180
gtttcttatc aacactgaaa natcaaagga aaaaatggt atcaagcatt acggaccatc    240
atacatcagc agaaataacc ataacaatta aattaatgca atgcattttc aggtctatgt    300
ttttacaaag tcggctgaac aagcaaaaga agatgctcc atagtaattt cacccaaaag    360
atagcataaa taatcagggt aaatatgcaa tgtaccagct aaagtcaaag gagaacaata    420
ccttggcagg atcatgtgta ttatttctca tgaaaagggg ggaagtccaa aaacattaca    480
atggaggaaa taacgaacat gatgaaccaa gaaaacagat caaagccaac aatcatgact    540
ggataatatg gcatgcatat attgttttag tttccaataa ttatcaaaat tttgaagcac    600
aacagaaaaa tatgcatcta tcactgatgc caaaacgaac acaatggaaa agaaaagca    660 aataaaaatc agttgaagag gggaattaac aaccttggta tgaggccaaa gttgatcagg    720
agatacatgc atagtgcaac cctctttacc agactcccat tcaacaacaa aacgagcaag    780
gacacctgaa ccaaagctaa accacaagct catcagtcca actgcctcaa ttctaaacgc    840
ccttctcatc tgttcagtta gtttgt                                         866

<210> SEQ ID NO 7
<211> LENGTH: 301
<212> TYPE: DNA
<213> ORGANISM: Glycine max
<220> FEATURE:
```

```
<221> NAME/KEY: misc_feature
<222> LOCATION: (201)..(201)
<223> OTHER INFORMATION: n is a, c, g, or t

<400> SEQUENCE: 7
cccacgttag tttctccgaa tcattcattc ttccacttac gctaatttct ctcctctgcg    60
atacaaaatc cctgcagtac cgttaaacga aaaaacaaaa aaggctcacg agtaacaaaa   120
gcttttgcaa ttttttttt ttaagtaaaa agaaaaaaaa gaatcagatt tcctagtacg    180
ctccagttac cggacacact naattttgaa gaaaatgaag gagagaaata aagaaaattt   240
aatcggtaat attttaaagt tatgtgcatg tggggagagt gaatgaattt gacaaattct   300
g                                                                  301

<210> SEQ ID NO 8
<211> LENGTH: 301
<212> TYPE: DNA
<213> ORGANISM: Glycine max
<220> FEATURE:
<221> NAME/KEY: misc_feature
<222> LOCATION: (201)..(201)
<223> OTHER INFORMATION: n is a, c, g, or t

<400> SEQUENCE: 8
gaagagcaaa atgacaacac tgaaaaaaaa cctaattgaa atacactaac aatataaaga   60 tttttaagt tataattcaa tcacaaatag ctatggtagg ttcgctgact attataataa    120
ctagtaactt ccttaaaact caggttttct acattatcat ttaaccacag attggtaagt   180
gttctggacc agccttcaac ngttcaacct actgccttcc tccgctccac cgccttacat   240
gttggccacg aaagccagat tcaggacatt gttaagtctt ggattcagga gtgacattga   300
a                                                                  301

<210> SEQ ID NO 9
<211> LENGTH: 25
<212> TYPE: DNA
<213> ORGANISM: Glycine max

<400> SEQUENCE: 9
ggtagctatc ctcaattggg tcatt                                         25

<210> SEQ ID NO 10
<211> LENGTH: 22
<212> TYPE: DNA
<213> ORGANISM: Glycine max

<400> SEQUENCE: 10
agccgtgccc ttctctagtt at                                            22

<210> SEQ ID NO 11
<211> LENGTH: 21
<212> TYPE: DNA
<213> ORGANISM: Glycine max

<400> SEQUENCE: 11
cctagggagg cgttctttct g                                             21

<210> SEQ ID NO 12
<211> LENGTH: 25
<212> TYPE: DNA
<213> ORGANISM: Glycine max

<400> SEQUENCE: 12
```

```
gggatgttcc gacagaatac tctct                                          25

<210> SEQ ID NO 13
<211> LENGTH: 28
<212> TYPE: DNA
<213> ORGANISM: Glycine max

<400> SEQUENCE: 13
catacatcag cagaaataac cataacaa                                       28

<210> SEQ ID NO 14
<211> LENGTH: 25
<212> TYPE: DNA
<213> ORGANISM: Glycine max

<400> SEQUENCE: 14
gatttcctag tacgctccag ttacc                                          25

<210> SEQ ID NO 15
<211> LENGTH: 25
<212> TYPE: DNA
<213> ORGANISM: Glycine max

<400> SEQUENCE: 15
cggctgcata aatacccaaa tcaat                                          25

<210> SEQ ID NO 16
<211> LENGTH: 24
<212> TYPE: DNA
<213> ORGANISM: Glycine max

<400> SEQUENCE: 16
gctatggtag gttcgctgac tatt                                           24

<210> SEQ ID NO 17
<211> LENGTH: 26
<212> TYPE: DNA
<213> ORGANISM: Glycine max

<400> SEQUENCE: 17
cgctcaagtt agtttaatcc gaagtg                                         26

<210> SEQ ID NO 18
<211> LENGTH: 26
<212> TYPE: DNA
<213> ORGANISM: Glycine max

<400> SEQUENCE: 18
agcttcagag tagatggtga gatgat                                         26

<210> SEQ ID NO 19
<211> LENGTH: 27
<212> TYPE: DNA
<213> ORGANISM: Glycine max

<400> SEQUENCE: 19
gccattagac tttcttctat caggaaa                                        27

<210> SEQ ID NO 20
<211> LENGTH: 27
<212> TYPE: DNA
<213> ORGANISM: Glycine max
```

```
<400> SEQUENCE: 20
tgcagatcct tctttcatct tcttgtt                                27

<210> SEQ ID NO 21
<211> LENGTH: 25
<212> TYPE: DNA
<213> ORGANISM: Glycine max

<400> SEQUENCE: 21
cttgttcagc cgactttgta aaaac                                  25

<210> SEQ ID NO 22
<211> LENGTH: 25
<212> TYPE: DNA
<213> ORGANISM: Glycine max

<400> SEQUENCE: 22
ctctccccac atgcacataa cttta                                  25

<210> SEQ ID NO 23
<211> LENGTH: 36
<212> TYPE: DNA
<213> ORGANISM: Glycine max

<400> SEQUENCE: 23
gatttgattt tactagatta atctgtcgag aaactg                      36

<210> SEQ ID NO 24
<211> LENGTH: 19
<212> TYPE: DNA
<213> ORGANISM: Glycine max

<400> SEQUENCE: 24
gagcggagga aggcagtag                                         19

<210> SEQ ID NO 25
<211> LENGTH: 17
<212> TYPE: DNA
<213> ORGANISM: Glycine max

<400> SEQUENCE: 25
atgtttaagg aagatac                                           17

<210> SEQ ID NO 26
<211> LENGTH: 16
<212> TYPE: DNA
<213> ORGANISM: Glycine max

<400> SEQUENCE: 26
cactgatgta tcaaat                                            16

<210> SEQ ID NO 27
<211> LENGTH: 18
<212> TYPE: DNA
<213> ORGANISM: Glycine max

<400> SEQUENCE: 27
tgagtgtgac attactag                                          18

<210> SEQ ID NO 28
<211> LENGTH: 17
<212> TYPE: DNA
<213> ORGANISM: Glycine max
```

```
<400> SEQUENCE: 28
atgacctttt atttaac                                              17

<210> SEQ ID NO 29
<211> LENGTH: 15
<212> TYPE: DNA
<213> ORGANISM: Glycine max

<400> SEQUENCE: 29
tgcattgcat taatt                                                15

<210> SEQ ID NO 30
<211> LENGTH: 17
<212> TYPE: DNA
<213> ORGANISM: Glycine max

<400> SEQUENCE: 30
cttcaaaatt gagtgtg                                              17

<210> SEQ ID NO 31
<211> LENGTH: 17
<212> TYPE: DNA
<213> ORGANISM: Glycine max

<400> SEQUENCE: 31
agattgaggt tcactaa                                              17

<210> SEQ ID NO 32
<211> LENGTH: 15
<212> TYPE: DNA
<213> ORGANISM: Glycine max

<400> SEQUENCE: 32
cttcaacagt tcaac                                                15

<210> SEQ ID NO 33
<211> LENGTH: 17
<212> TYPE: DNA
<213> ORGANISM: Glycine max

<400> SEQUENCE: 33
atgtttaagg gagatac                                              17

<210> SEQ ID NO 34
<211> LENGTH: 15
<212> TYPE: DNA
<213> ORGANISM: Glycine max

<400> SEQUENCE: 34
actgatgtgt caaat                                                15

<210> SEQ ID NO 35
<211> LENGTH: 16
<212> TYPE: DNA
<213> ORGANISM: Glycine max

<400> SEQUENCE: 35
agtgtggcat tactag                                               16

<210> SEQ ID NO 36
<211> LENGTH: 16
<212> TYPE: DNA
```

```
<213> ORGANISM: Glycine max

<400> SEQUENCE: 36 tgacctttg tttaac                                                       16

<210> SEQ ID NO 37
<211> LENGTH: 16
<212> TYPE: DNA
<213> ORGANISM: Glycine max

<400> SEQUENCE: 37
ctgaaaatgc atcgca                                                      16

<210> SEQ ID NO 38
<211> LENGTH: 17
<212> TYPE: DNA
<213> ORGANISM: Glycine max

<400> SEQUENCE: 38
cttcaaaatt cagtgtg                                                     17

<210> SEQ ID NO 39
<211> LENGTH: 15
<212> TYPE: DNA
<213> ORGANISM: Glycine max

<400> SEQUENCE: 39
attgaggctc actaa                                                       15

<210> SEQ ID NO 40
<211> LENGTH: 14
<212> TYPE: DNA
<213> ORGANISM: Glycine max

<400> SEQUENCE: 40
ttcaacggtt caac                                                        14
```